(12) United States Patent
Ternes et al.

(10) Patent No.: US 11,931,580 B2
(45) Date of Patent: Mar. 19, 2024

(54) DOSED DELIVERY OF AUTONOMIC MODULATION THERAPY

(71) Applicant: Cardiac Pacemakers, Inc., St. Paul, MN (US)

(72) Inventors: David J. Ternes, Roseville, MN (US); Jason J. Hamann, Blaine, MN (US); Stephen B. Ruble, Lino Lakes, MN (US); Juan Gabriel Hincapie Ordonez, Maple Grove, MN (US); Manfred Franke, Weissenborn Sa. (DE)

(73) Assignee: Cardiac Pacemakers, Inc., St. Paul, MN (US)

( * ) Notice: Subject to any disclaimer, the term of this patent is extended or adjusted under 35 U.S.C. 154(b) by 634 days.

(21) Appl. No.: 16/526,750

(22) Filed: Jul. 30, 2019

(65) Prior Publication Data
US 2019/0351238 A1    Nov. 21, 2019

Related U.S. Application Data

(63) Continuation of application No. 15/369,664, filed on Dec. 5, 2016, now Pat. No. 10,391,323, which is a
(Continued)

(51) Int. Cl.
*A61N 1/372*    (2006.01)
*A61N 1/36*    (2006.01)

(52) U.S. Cl.
CPC ...... *A61N 1/36135* (2013.01); *A61N 1/36114* (2013.01); *A61N 1/3727* (2013.01)

(58) Field of Classification Search
CPC .............. A61N 1/0551; A61N 1/36139; A61N 1/36135; A61N 1/36167; A61N 1/3702;
(Continued)

(56) References Cited

U.S. PATENT DOCUMENTS 7,321,793 B2    1/2008  Ben Ezra et al.
7,542,800 B2    6/2009  Libbus et al.
(Continued)

FOREIGN PATENT DOCUMENTS

CN    102958563 A    3/2013
CN    105813687 A    7/2016
(Continued)

OTHER PUBLICATIONS

"U.S. Appl. No. 14/557,667, Advisory Action dated Mar. 2, 2016", 5 pgs.
(Continued)

*Primary Examiner* — Deborah L Malamud
(74) *Attorney, Agent, or Firm* — Schwegman Lundberg & Woessner, P.A.

(57) ABSTRACT

An example of a method embodiment may include receiving a user programmable neural stimulation (NS) dose for an intermittent neural stimulation (INS) therapy, and delivering the INS therapy with the user programmable NS dose to an autonomic neural target of a patient. Delivering the INS therapy may include delivering NS bursts, and delivering the NS bursts may include delivering a number of NS pulses per cardiac cycle during a portion of the cardiac cycles and not delivering NS pulses during a remaining portion of the cardiac cycles. The method may further include sensing cardiac events within the cardiac cycles, and controlling delivery of the user programmable NS dose of INS therapy using the sensed cardiac events to time delivery of the number of NS pulses per cardiac cycle to provide the user programmable NS dose. The user programmable NS dose may determine the number of NS pulses per cardiac cycle.

20 Claims, 9 Drawing Sheets

Related U.S. Application Data continuation of application No. 14/557,667, filed on Dec. 2, 2014, now Pat. No. 9,517,350.

(60) Provisional application No. 61/912,274, filed on Dec. 5, 2013.

(58) Field of Classification Search
CPC ........ A61N 1/3605; A61N 1/37; A61N 1/365; A61N 1/36146; A61N 1/08; A61N 1/36178; A61B 5/4035; A61B 5/024; A61B 5/0452; A61B 5/4836
See application file for complete search history.

(56) References Cited

U.S. PATENT DOCUMENTS

| | | | |
|---|---|---|---|
| 7,729,760 B2 * | 6/2010 | Patel | A61N 1/36082 607/2 |
| 7,974,693 B2 | 7/2011 | Ben-David et al. | |
| 8,219,188 B2 | 7/2012 | Craig | |
| 8,285,373 B2 | 10/2012 | Ternes et al. | |
| 8,805,502 B2 | 8/2014 | Ternes et al. | |
| 9,370,659 B2 | 6/2016 | Franke et al. | |
| 9,517,350 B2 | 12/2016 | Ternes et al. | |
| 10,391,323 B2 | 8/2019 | Ternes et al. | |
| 2006/0224188 A1 | 10/2006 | Libbus et al. | |
| 2012/0185010 A1 | 7/2012 | Zhou et al. | |
| 2015/0157867 A1 | 6/2015 | Ternes et al. | |
| 2015/0157868 A1 | 6/2015 | Franke et al. | |
| 2017/0080238 A1 | 3/2017 | Ternes et al. | |

FOREIGN PATENT DOCUMENTS

| | | |
|---|---|---|
| CN | 105813687 B | 3/2018 |
| EP | 3077044 B1 | 8/2018 |
| WO | WO-03099373 A2 | 12/2003 |
| WO | WO-03099377 A1 | 12/2003 |
| WO | WO-2015084774 A1 | 6/2015 |

OTHER PUBLICATIONS

"U.S. Appl. No. 14/557,667, Final Office Action dated Dec. 23, 2015", 7 pgs.
"U.S. Appl. No. 14/557,667, Non Final Office Action dated Apr. 18, 2016", 8 pgs.
"U.S. Appl. No. 14/557,667, Non Final Office Action dated Aug. 20, 2015", 8 pgs.
"U.S. Appl. No. 14/557,667, Notice of Allowance dated Aug. 4, 2016", 7 pgs.
"U.S. Appl. No. 14/557,667, Response filed Feb. 22, 2016 to Final Office Action dated Dec. 23, 2015", 14 pgs.
"U.S. Appl. No. 14/557,667, Response filed Mar. 23, 2016 to Advisory Action dated Mar. 2, 2016", 11 pgs.
"U.S. Appl. No. 14/557,667, Response filed Jul. 18, 2016 to Non Final Office Action dated Apr. 18, 2016", 10 pgs.
"U.S. Appl. No. 14/557,667, Response filed Nov. 19, 2015 to Non Final Office Action dated Aug. 20, 2015", 11 pgs.
"U.S. Appl. No. 14/557,707, Final Office Action dated Dec. 15, 2015", 7 pgs.
"U.S. Appl. No. 14/557,707, Non Final Office Action dated Aug. 20, 2015", 8 pgs.
"U.S. Appl. No. 14/557,707, Notice of Allowance dated Feb. 24, 2016", 7 pgs.
"U.S. Appl. No. 14/557,707, Response filed Feb. 11, 2016 to Final Office Action dated Dec. 15, 2015", 9 pgs.
"U.S. Appl. No. 14/557,707, Response filed Nov. 19, 2015 to Non Final Office Action dated Aug. 20, 2015", 9 pgs.
"U.S. Appl. No. 15/369,664, Corrected Notice of Allowability dated May 30, 2019", 4 pgs.
"U.S. Appl. No. 15/369,664, Final Office Action dated Nov. 6, 2018", 9 pgs.
"U.S. Appl. No. 15/369,664, Non Final Office Action dated Jun. 13, 2018", 9 pgs.
"U.S. Appl. No. 15/369,664, Notice of Allowance dated Apr. 11, 2019", 17 pgs.
"U.S. Appl. No. 15/369,664, Response filed Sep. 12, 2018 to Non Final Office Action dated Jun. 13, 2018", 12 pgs.
"U.S. Appl. No. 15/369,664, Response filed Mar. 6, 2019 to Final Office Action dated Nov. 6, 2018", 12 pgs.
"U.S. Appl. No. 15/369,664, Restriction Requirement dated Mar. 19, 2018", 6 pgs.
"Chinese Application Serial No. 201480066417.6, Office Action dated Jun. 26, 2017", w/ English translation, 19 pgs.
"Chinese Application Serial No. 201480066417.6, Response filed Nov. 7, 2017 to Office Action dated Jun. 26, 2017", w/ claims in English, 48 pgs.
"European Application Serial No. 14815542.7, Response filed Jan. 19, 2017 to Communication Pursuant to Rules 161(1) and 162 EPC dated Jul. 13, 2016", 5 pgs.
"International Application Serial No. PCT/US2014/068028, International Preliminary Report on Patentability dated Jun. 16, 2016", 5 pgs.
"International Application Serial No. PCT/US2014/068028, International Search Report dated Feb. 16, 2015", 3 pgs.
"International Application Serial No. PCT/US2014/068028, Written Opinion dated Feb. 16, 2015", 3 pgs.
Barrett, D. J., et al., "Spontaneous efferent activity in branches of the vagus nerve controlling heart rate and ventilation in the dogfish", J. exp. Biol. 117, (1985), 433-448.
Green, J. H., et al., "Studies Upon the Relationship Between Baroreceptor and Sympathetic Activity", Q. Ji exp. Physiol. (1968) 53, (1968), 23-32.
Sung J., et al., "Exercise blood pressure response is related to left ventricular mass", Journal of Human Hypertension (2003) 17, 333-338, (2003), 333-338.

* cited by examiner

DOSED DELIVERY OF AUTONOMIC MODULATION THERAPY

CLAIM OF PRIORITY

This application is a continuation of U.S. application Ser. No. 15/369,664, filed Dec. 5, 2016, which is a continuation of U.S. application Ser. No. 14/557,667, filed Dec. 2, 2014, now issued as U.S. Pat. No. 9,517,350, which claims the benefit of priority under 35 U.S.C. § 119(e) of U.S. Provisional Patent Application Ser. No. 61/912,274, filed on Dec. 5, 2013, which is herein incorporated by reference in its entirety.

TECHNICAL FIELD

This document relates generally to medical devices, and more particularly, to systems, devices and methods for delivering electrical stimulation.

BACKGROUND

Neural stimulation has been proposed as a therapy for a number of conditions. Neural stimulation may be delivered to modulate the autonomic system, which may be referred to as an autonomic modulation therapy (AMT). Examples of AMT include therapies for respiratory problems such as sleep disordered breathing, blood pressure control such as to treat hypertension, cardiac rhythm management, myocardial infarction and ischemia, heart failure (HF), epilepsy, depression, pain, migraines, eating disorders and obesity, and movement disorders.

AMT may be delivered using intermittently delivered bursts of neural stimulation pulses. The intensity of this stimulation may be determined by many stimulation parameters such as pulse width, pulse frequency, ON/OFF timing, and amplitude. What is needed is a more intuitive way of dosing AMT.

SUMMARY

Various embodiments provided herein may provide a simpler, intuitive way for dosing AMT by delivering AMT as a dose per cardiac cycle. An example of a method embodiment may include receiving a user programmable neural stimulation (NS) dose for an intermittent neural stimulation (INS) therapy, and delivering the INS therapy with the user programmable NS dose to an autonomic neural target of a patient. Delivering the INS therapy may include delivering NS bursts, and delivering the NS bursts may include delivering a number of NS pulses per cardiac cycle during a portion of the cardiac cycles and not delivering NS pulses during a remaining portion of the cardiac cycles. The method may further include sensing cardiac events within the cardiac cycles, and controlling delivery of the user programmable NS dose of INS therapy using the sensed cardiac events to time delivery of the number of NS pulses per cardiac cycle to provide the user programmable NS dose. The user programmable NS dose may determine the number of NS pulses per cardiac cycle.

An example of a method embodiment for programming a neural stimulator to deliver intermittent neural stimulation (INS) to an autonomic neural target of a patient, where the INS therapy includes neural stimulation (NS) ON times alternating with NS OFF times, may include programming a value in units of NS pulses per cardiac cycle for an programmable NS dose parameter for the INS therapy. The INS therapy may include an NS burst of NS pulses during a portion of the cardiac cycle corresponding to one of the NS ON times and no NS pulses during a remaining portion of the cardiac cycle corresponding to one of the NS OFF times. The number of pulses in the NS burst may be the number of NS pulses per cardiac cycle. Some embodiments may further include programming the pulse amplitude for the burst of pulses.

An example of a system may include a cardiac cycle monitor, a neural stimulator, a memory and a communication system. The cardiac cycle monitor may be configured to monitor cardiac events within cardiac cycles. The neural stimulator may be configured to deliver neural stimulation (NS) to the autonomic neural target. The memory may be configured to store a programmable NS dose parameter for an intermittent neural stimulation (INS) therapy. The programmable NS dose parameter may include a value for a number of NS pulses per cardiac cycle. The communication system may be configured to receive programming instructions for the NS dose parameter including the value for the number of NS pulses per cardiac cycle, and store the value for the number of NS pulses per cardiac cycle in the memory. The controller may be configured to control the neural stimulator to deliver the INS therapy to the autonomic neural target. The controller, the memory, the neural stimulator and the cardiac cycle monitor may be configured to cooperate to implement a process to deliver the INS therapy where the process includes sensing a cardiac event within a cardiac cycle; and delivering NS bursts of NS pulses. Delivering NS bursts may include timing delivery of the NS bursts using the sensed cardiac events within the cardiac cycles. The number of NS pulses per cardiac cycle may be delivered during a first portion of a cardiac cycle, and the remaining portion of the cardiac cycle may be without NS pulses.

This Summary is an overview of some of the teachings of the present application and not intended to be an exclusive or exhaustive treatment of the present subject matter. Further details about the present subject matter are found in the detailed description and appended claims. Other aspects of the disclosure will be apparent to persons skilled in the art upon reading and understanding the following detailed description and viewing the drawings that form a part thereof, each of which are not to be taken in a limiting sense. The scope of the present disclosure is defined by the appended claims and their legal equivalents.

BRIEF DESCRIPTION OF THE DRAWINGS

Various embodiments are illustrated by way of example in the figures of the accompanying drawings. Such embodiments are demonstrative and not intended to be exhaustive or exclusive embodiments of the present subject matter.

DETAILED DESCRIPTION

Figure 1:
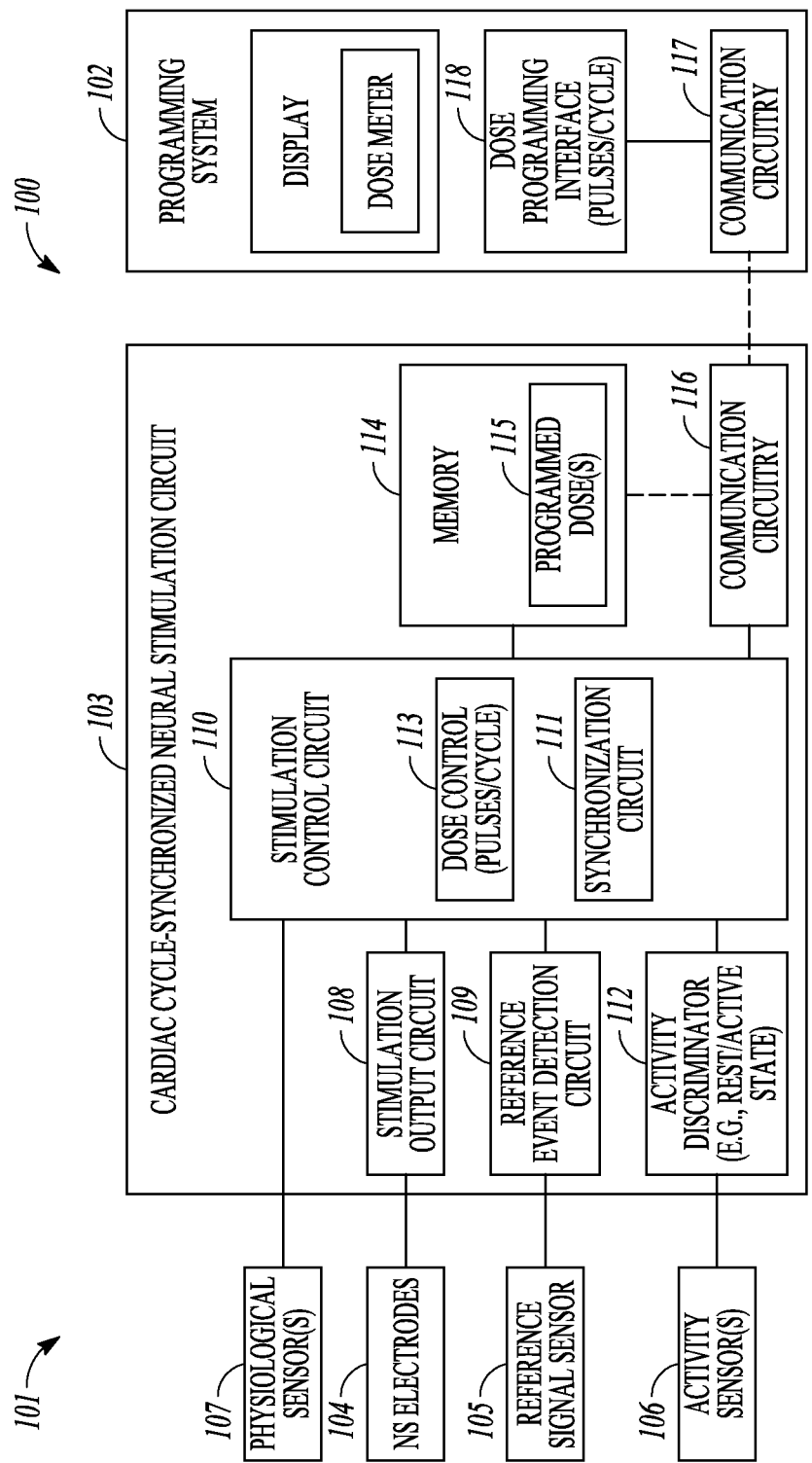
FIG. 1 illustrates, by way of example, an embodiment of a system that provides neural stimulation hat is synchronized to the cardiac cycle and that uses using an NS dose of pulses per cardiac cycle.

The following detailed description of the present subject matter refers to the accompanying drawings which show, by way of illustration, specific aspects and embodiments in which the present subject matter may be practiced. These embodiments are described in sufficient detail to enable those skilled in the art to practice the present subject matter. Other embodiments may be utilized and structural, logical, and electrical changes may be made without departing from the scope of the present subject matter. For example, neural stimulation as used herein may refer to stimulation that elicits nerve traffic in a neural target. However, a neural target may be stimulated with appropriate stimulation parameters to reduce or block nerve traffic at the neural target. References to "an", "one", or "various" embodiments in this disclosure are not necessarily to the same embodiment, and such references contemplate more than one embodiment. The following detailed description is, therefore, not to be taken in a limiting sense, and the scope is defined only by the appended claims, along with the full scope of legal equivalents to which such claims are entitled.

Neural stimulation may be delivered to stimulate the autonomic nervous system (ANS). For example, the neural stimulation may be directed to stimulating a vagus nerve in the neck (e.g. cervical vagus nerve) or to stimulating various nerves that branch from the vagus nerve trunk. The neural stimulation may be directed to other autonomic nervous system targets. Examples of other autonomic neural stimulation targets include but are not limited to baroreceptor regions such as may be found in the carotid sinus region or in the pulmonary artery, chemoreceptor regions, the glossopharyngeal nerve, the carotid sinus nerve, and spinal nerves. The ANS regulates "involuntary" organs. Examples of involuntary organs include respiratory and digestive organs, and also include blood vessels and the heart. Often, the ANS functions in an involuntary, reflexive manner to regulate glands, to regulate muscles in the skin, eye, stomach, intestines and bladder, and to regulate cardiac muscle and the muscles around blood vessels, for example.

The ANS includes the sympathetic nervous system and the parasympathetic nervous system. The sympathetic nervous system is affiliated with stress and the "fight or flight response" to emergencies. Among other effects, the "fight or flight response" increases blood pressure and heart rate to increase skeletal muscle blood flow, and decreases digestion to provide the energy for "fighting or fleeing." The parasympathetic nervous system is affiliated with relaxation and the "rest and digest response" which, among other effects, decreases blood pressure and heart rate, and increases digestion to conserve energy. The ANS maintains normal internal function and works with the somatic nervous system. Afferent neurons convey impulses towards the central nervous system (CNS), and efferent neurons convey impulses away from the CNS.

Stimulating the sympathetic and parasympathetic nervous systems can cause heart rate, blood pressure and other physiological responses. For example, stimulating the sympathetic nervous system may dilate the pupil, reduce saliva and mucus production, relax the bronchial muscle, reduce the successive waves of involuntary contraction (peristalsis) of the stomach and the motility of the stomach, increase the conversion of glycogen to glucose by the liver, decrease urine secretion by the kidneys, and relax the wall and closes the sphincter of the bladder. Stimulating the parasympathetic nervous system (inhibiting the sympathetic nervous system) may constrict the pupil, increase saliva and mucus production, contract the bronchial muscle, increase secretions and motility in the stomach and large intestine, increase digestion in the small intestine, increase urine secretion, and contract the wall and relax the sphincter of the bladder. The functions associated with the sympathetic and parasympathetic nervous systems are many and can be complexly integrated with each other. A therapy which intentionally affects the parasympathetic activity and/or sympathetic activity within the ANS may be referred to as an Autonomic Modulation Therapy (AMT). A neural stimulation therapy delivered to an autonomic neural target is an example of an AMT. The vagus nerve is an example of an autonomic neural target. For example, the cervical vagus nerve may be stimulated to treat conditions such as, by way of example and not limitation, hypertension, heart failure, arrhythmias and pain. Other examples of conditions that may be treatable using vagus nerve stimulation include, but are not limited to, migraines, eating disorders, obesity, inflammatory diseases, and movement disorders. Other autonomic neural targets include, but are not limited to, baroreceptor regions, chemoreceptor regions, cardiac fat pads, various branches of the vagus nerve, the carotid sinus nerve, and the glossopharyngeal nerve.

A reduction in parasympathetic nerve activity contributes to the development and progression of a variety of cardiovascular diseases. Some embodiments of the present subject matter can be used to prophylactically or therapeutically treat various cardiovascular diseases by modulating autonomic tone. Neural stimulation to treat cardiovascular diseases may be referred to as neurocardiac therapy (NCT). Vagal stimulation used to treat cardiovascular diseases may be referred to as either vagal stimulation therapy (VST) or NCT. However, VST may be delivered for non-cardiovascular diseases, and NCT may be delivered by stimulating a nerve other than the vagal nerve. Examples of cardiovascular diseases or conditions that may be treated using AMT include hypertension, HF, and cardiac remodeling. These conditions are briefly described below.

Hypertension is a cause of heart disease and other related cardiac co-morbidities. Hypertension occurs when blood vessels constrict. As a result, the heart works harder to maintain flow at a higher blood pressure, which can contribute to HF. Hypertension generally relates to high blood pressure, such as a transitory or sustained elevation of systemic arterial blood pressure to a level that is likely to induce cardiovascular damage or other adverse consequences. Hypertension has been defined as a systolic blood pressure above 140 mm Hg or a diastolic blood pressure above 90 mm Hg. Consequences of uncontrolled hypertension include, but are not limited to, retinal vascular disease and stroke, left ventricular hypertrophy and failure, myocardial infarction, dissecting aneurysm, and renovascular disease. A large segment of the general population, as well as a large segment of patients implanted with pacemakers or defibrillators, suffer from hypertension. The long term mortality as well as the quality of life can be improved for this population if blood pressure and hypertension can be reduced. Many patients who suffer from hypertension do not respond to treatment, such as treatments related to lifestyle changes and hypertension drugs.

HF refers to a clinical syndrome in which cardiac function causes a below normal cardiac output that can fall below a level adequate to meet the metabolic demand of peripheral tissues. HF may present itself as congestive heart failure (CHF) due to the accompanying venous and pulmonary congestion. HF can be due to a variety of etiologies such as ischemic heart disease. HF patients have impaired autonomic balance, which is associated with LV dysfunction and increased mortality.

Cardiac remodeling refers to a complex remodeling process of the ventricles that involves structural, biochemical, neurohormonal, and electrophysiologic factors, which can result following a myocardial infarction (MI) or other cause of decreased cardiac output. Ventricular remodeling is triggered by a physiological compensatory mechanism that acts to increase cardiac output due to so-called backward failure which increases the diastolic filling pressure of the ventricles and thereby increases the so-called preload (i.e., the degree to which the ventricles are stretched by the volume of blood in the ventricles at the end of diastole). An increase in preload causes an increase in stroke volume during systole, a phenomena known as the Frank-Starling principle. When the ventricles are stretched due to the increased preload over a period of time, however, the ventricles become dilated. The enlargement of the ventricular volume causes increased ventricular wall stress at a given systolic pressure. Along with the increased pressure-volume work done by the ventricle, this acts as a stimulus for hypertrophy of the ventricular myocardium. The disadvantage of dilatation is the extra workload imposed on normal, residual myocardium and the increase in wall tension (Laplace's Law) which represent the stimulus for hypertrophy. If hypertrophy is not adequate to match increased tension, a vicious cycle ensues which causes further and progressive dilatation. As the heart begins to dilate, afferent baroreceptor and cardiopulmonary receptor signals are sent to the vasomotor central nervous system control center, which responds with hormonal secretion and sympathetic discharge. The combination of hemodynamic, sympathetic nervous system and hormonal alterations (such as presence or absence of angiotensin converting enzyme (ACE) activity) account for the deleterious alterations in cell structure involved in ventricular remodeling. The sustained stresses causing hypertrophy induce apoptosis (i.e., programmed cell death) of cardiac muscle cells and eventual wall thinning which causes further deterioration in cardiac function. Thus, although ventricular dilation and hypertrophy may at first be compensatory and increase cardiac output, the processes ultimately result in both systolic and diastolic dysfunction. It has been shown that the extent of ventricular remodeling is positively correlated with increased mortality in post-MI and heart failure patients.

It has been proposed to deliver bursts of neural stimulation pulses synchronized to a cardiac cycle. One example of such a system is provided in U.S. application Ser. No. 61/912,315, filed on the Dec. 5, 2013, and entitled "Intuited Delivery of Autonomic Modulation Therapy," which application is incorporated by reference herein in its entirety. Thus, for example, various embodiments described herein may deliver estimate cardiac timing.

Various embodiments provided herein use a dose per cardiac cycle to deliver AMT. For example, the dose per cardiac cycle may simply be controlled using the number of pulses to be delivered within a cardiac cycle. A benefit of such an approach is more intuitive programming that can reduce the number of programmed parameters. For example if the number of pulses per cardiac cycle is preprogrammed, the clinician may only need to program amplitude to control the intensity of AMT. In some embodiments the clinician is able to control the number of pulses delivered per cardiac cycle. In some embodiments, the clinician may be able to program both the number of pulses delivered per cardiac cycle and amplitude of the pulses.

Additionally, lower frequencies may be more tolerable for patients at rest, and patients are mostly at rest. Further, it is believed that patients may better tolerate AMT delivered with an increased frequency when active. As an exaggerated systolic blood pressure response to exercise may be associated with increased left ventricular mass, it may be desirable to increase VNS or other AMT that elicits a parasympathetic response to counter to blood pressure response.

Some embodiments may be configured to mimic healthy nerve activity response to cardiac activity. For example, "n" pulses may be delivered within natural cardiac tissue refractory period. Some embodiments may adjust the stimulation to account for changes in the cardiac cycle as rate changes. For example, the refractory period decreases as the intrinsic or paced heart rate increases. Some system embodiments automatically adjust the frequency of AMT burst delivery to distribute the pulses during the tissue refractory to maintain same number of pulses delivered within tissue refractory and/or device sense refractory windows.

The intuitive programming may use several pre-set program modes. For example, a nominal mode such as but not limited to two pulses per cycle and a high output mode such as but not limited to four pulses per cycle may be used. A dynamic mode may be used to switch between two modes or among more than two modes. For example, two pulses per cycle may be delivered during a resting state and four pulses per cycle may be delivered during an active state. The modes may switch based on activity, rate, and/or minute ventilation (MV) sensing, by way of example and not limitation.

The number of pulses per cardiac cycle may increase as rate goes down. Furthermore, there may be no change in the pulse frequency of the burst of pulses. As the rate goes down, the window of time (e.g. refractory period) for delivering pulses may increase.

The number of pulses per cardiac cycle may decrease as rate goes down. There is less intrinsic sympathetic activity at lower rates. Thus, a therapy that mimics or follows the intrinsic sympathetic activity may deliver fewer pulses per cardiac cycle for lower cardiac rates. Furthermore, there may be no change in pulse frequency with the fewer pulses. The reduced number of pulses at resting rates may be more tolerable. Additionally, as a patient is usually at a resting rate, the reduced number of delivered pulses may increase the life of a battery-powered neural stimulator.

A dynamic system may adjust both the number of pulses and the pulse frequency. For example, a dynamic system may increase the number of pulses per cycle with an increasing rate, and increase the frequency between pulses with increasing rate to stay within shrinking refractory window.

A dynamic system may change one or more neural stimulation parameters based on heart rate, or activity or a blended sensor that has heart rate and activity inputs. These neural stimulation parameters may include one or more of a pulse width, an amplitude, a product of pulse width and amplitude (e.g. product=pulse width*amplitude), and pulse frequency.

Some embodiments may program the duty cycle based on cardiac cycles. By way of example and not limitation, the system may be programmed to provide a stimulation ON portion of the duty cycle for 10 cardiac cycles, and to provide a stimulation OFF portion of the duty cycle for 50 cardiac cycles. This programmed duty cycle may be adjusted based on a detected heart rate. For example, the number of cardiac cycles may be decreased as rate increases. For example, the decrease may be used to maintain the average amount of charge delivered over a period of time (e.g. minute). By way of example and not limitation, if the system is programmed with a stimulation ON portion of the duty cycle of 10 cardiac cycles and a stimulation OFF portion of the duty cycle of 50 cardiac cycles at a heart rate of 60 beats per minute, the system may be programmed to respond to a detected heart rate of 120 beats per minute by changing the stimulation ON portion of the duty cycle to 5 cardiac cycles and the stimulation OFF portion of the duty cycle to 55 cardiac cycles. Thus, assuming the pulse width does not change, the energy delivered over one minute remains the same whether the heart rate is 60 beats per minute (e.g. 10 pulses delivered during the first 10 cardiac cycles from about time 0 seconds to about 10 seconds) or 120 beats per minutes (e.g. 5 pulses delivered during the first five cardiac cycles from about 0 seconds to about 2.5 seconds and 5 pulses delivered during the $60^{th}$ to $65^{th}$ cardiac cycles from about 30 seconds to about 32.5 seconds).

The dose of cardiac pulses may be delivered at a specific time, or times, within the cardiac cycle. Thus, various embodiments may determine a cardiac event and use the cardiac event to time the delivery of the NS burst of pulses. A cardiac event may be determined by ECG, monitored blood pressure wave (plethysmography), heart sounds, carotid sounds, cardiac pace detection (nearly 100% of cardiac cycles for CRT), info transferred from other device (external, ICD, pressure monitor, etc.). These examples are provided as non-limiting examples. A cardiac "event" may be a "time-out" from the last detected cardiac event, similar to a lower rate limit (LRL) for a cardiac rhythm management (CRM) device such as a pacemaker). Some detected cardiac events, such as a premature ventricular contraction (PVC), antitachycardia pacing (ATP), or a LRL may trigger a specific does with a frequency determined by cardiac rate. A current cardiac rate may be determined on a cycle by cycle basis (i.e. pacemaker-like) or based on an average of preceding cycles. For example, the cardiac rate may be based on last four cardiac cycles by way of example and not limitation. The average may be based on other number of cardiac cycles.

U.S. Pat. No. 7,542,800, entitled "Method and Apparatus for Synchronizing Neural Stimulation to Cardiac Cycles", assigned to Cardiac Pacemakers, Inc." discusses and example for synchronizing neural stimulation to cardiac cycle. U.S. Pat. No. 7,542,800 is incorporated by reference in its entirety. The present subject matter can be implemented within such a system, as it controls the NS dose delivered per cardiac cycle.

FIG. 1 illustrates, by way of example, an embodiment of a system that provides neural stimulation that is synchronized to the cardiac cycle and that uses an NS dose of pulses per cardiac cycle. The illustrated system 100 may include a first system 101, such as an implantable device, and a second system 102, such as an external device, used for programming the first device. The illustrated first system 101 may include a cardiac cycle-synchronized neural stimulation circuit 103, NS electrodes 104 for use in delivering neural stimulation, and a reference signal sensor 105 for use in detecting a reference within a cardiac cycle. Detection of the reference allows the circuit 103 to synchronize delivering of a burst of NS pulses within the cardiac cycle. The first system 101 may further include an activity sensor or sensors 106 and another physiological sensor or sensors 107 which may be used to provide feedback for a NS therapy delivered by the first system 101 or to sense and record diagnostic data for evaluation by a user of the system.

The reference signal sensor 105 senses a reference signal indicative of cardiac cycles. The reference signal sensor 105 may be an implantable reference signal sensor. The timing reference event is a recurring feature of the cardiac cycle that is chosen to be a timing reference to which the neural stimulation is synchronized. The reference signal sensor 105 may be configured for extracardiac and extravascular placement, i.e., placement external to the heart and blood vessels. Examples of reference signal sensors may include a set of electrodes for sensing a subcutaneous ECG signal, an acoustic sensor for sensing an acoustic signal indicative of heart sounds, and a hemodynamic sensor for sensing a hemodynamic signal indicative of hemodynamic performance. The first system 101 may have an implantable housing that contains both a reference signal sensor 105 and cardiac cycle-synchronized neural stimulation circuit 103. In an embodiment, reference signal sensor 105 is incorporated onto the implantable housing. In an embodiment, the reference signal sensor 105 is electrically connected to the first system 101 through one or more leads. In an embodiment, the reference signal sensor 105 may be communicatively coupled to first device or system 101 via an intra-body telemetry link.

The cardiac cycle-synchronized neural stimulation circuit 103 may include a stimulation output circuit 108, a reference event detection circuit 109, and a stimulation control circuit 110. The reference event detection circuit 109 receives the reference signal from reference signal sensor 105 and detects the timing reference event from the reference signal. The stimulation control circuit 110 controls the delivery of the neural stimulation pulses and includes a synchronization circuit 111. The synchronization circuit 111 may be configured to receive signal indicative of the detection of each timing reference event and synchronizes the delivery of the neural stimulation pulses to the detected timing reference event. The stimulation output circuit 108 may be configured to deliver neural stimulation pulses upon receiving a pulse delivery signal from the stimulation control circuit 110. The first system 101 may further include an activity discriminator 112 to determine an activity level based on the output from the activity sensor(s) 106. The stimulation control circuit 110 may include a dose control module 113 configured to control the NS dose by controlling the burst of NS pulses delivered per cardiac cycle. The stimulation control circuit 113 may use activity and/or other sensed physiological parameters to control the dose delivered per cardiac cycle.

The cardiac cycle-synchronized neural stimulation circuit 103 may include a memory 114 which may contained preprogrammed or user-programmable NS doses 115 for delivering one or more bursts of NS pulses within a cardiac cycle, and may further include communication circuitry 116 for use in communicating with the second system 102. The second system 102 has communication circuitry 117 for use in communication with the communication circuitry 116 of the first device or system 101. The second system 102 further includes a dose programming interface 118 for use by a user to program the dose(s) into the memory 114. The dose may be delivered as pulses per cardiac cycle. In some embodiments a desired number of pulses per cardiac cycle may be programmed as a desired dose. In some embodiments a maximum number of pulses per cycle may be programmed as a maximum dose where the system is configured to adjust the dose to allowable dosages less than the maximum dose. Furthermore, according to some embodiments a user may use the second device or system 102 to program a desired amplitude of the NS pulses delivered within an NS dose. Thus, the amplitude of the NS pulses may be a programmable parameter regardless of whether the number of pulses per cardiac cycle is a user-programmable value or a preprogrammed value. The second system 102 may also include a display, and may be configured to provide an indication to the physician how much stimulation is being delivered over a period of time. This indication may be referred to as a dose meter. The dose meter informs the physician how much stimulation (e.g. number of pulses, or total charge delivered) is or will be delivered. Various combinations of pulse parameters can be displayed to provide a calculated or estimated dose. For example, a product of amplitude and pulse number may be used to provide an estimate of the dose over the period of time. By way of example but not limitation, the period of time may be an hour or a day. Furthermore, the dose meter may provide current dose information that reflects the dose delivered using the currently-programmed stimulation parameters, and may also provide dose information for a proposed stimulation parameters which allows the physician to confirm the dose information before programming those parameters into the memory 114 of the first system 101.

Figure 2:
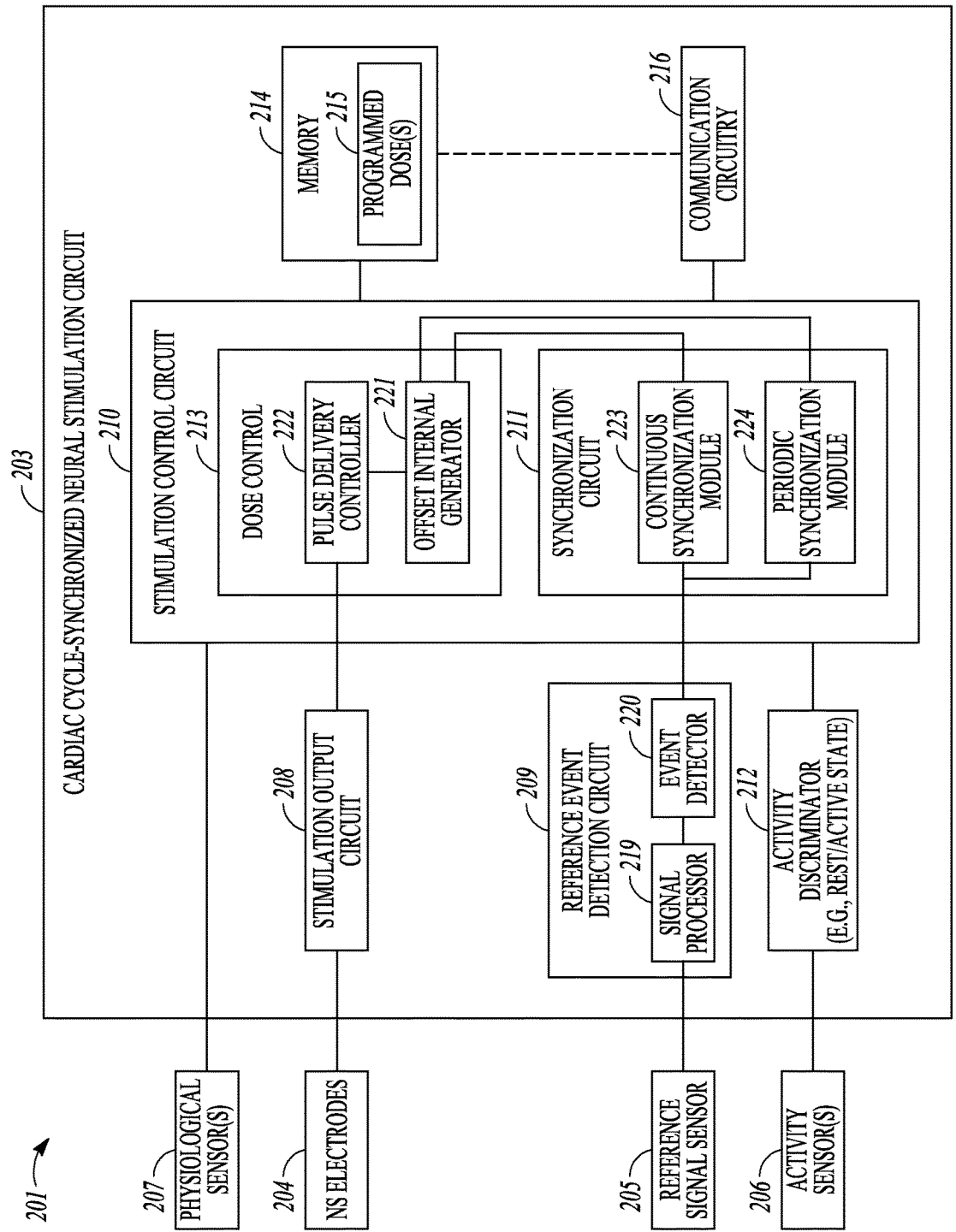
FIG. 2 illustrates an example of a system which may be a more specific embodiment of the system in FIG. 1.

FIG. 2 illustrates an example of a system which may be a more specific embodiment of the system in FIG. 1. The system 201 includes a cardiac cycle-synchronized neural stimulation circuit 203, which is a specific embodiment of the cardiac cycle-synchronized neural stimulation circuit 103 in FIG. 1. The cardiac cycle-synchronized neural stimulation circuit 203 includes a stimulation output circuit 208, a reference event detection circuit 209, and a stimulation control circuit 210.

The reference event detection circuit 209 may be a specific embodiment of the reference event detection 109 and includes a signal processor 219 and an event detector 220. The signal processor 219 receives the reference signal sensed by the reference signal sensor 205 and processes the reference signal in preparation for the detection of the timing reference events by event detector 220. The event detector 220 may include a comparator having an input to receive the processed reference signal, another input to receive a detection threshold, and an output producing a detection signal indicating a detection of the timing reference signal. In an embodiment, the signal processor 219 processes the reference signal to provide for extraction of the timing reference event based on a single cardiac cycle. In an embodiment, the signal processor 219 includes a filter having a pass-band corresponding to a frequency range of the timing reference event to prevent unwanted activities in the reference signal from being detected by event detector 220. In an embodiment, the signal processor 219 includes a blanking period generator to generate a blanking period that blanks the unwanted activities in the reference signal. This approach is applied when an approximate timing relationship between the timing reference event and the unwanted activities, or an approximate timing relationship between another detectable event and the unwanted activities, is predictable. In an embodiment, the blanking period generator generates a blanking period that blanks cardiac pacing artifacts in the reference signal, i.e., unwanted activities caused by delivery of cardiac pacing pulses. In an embodiment, the signal processor 219 includes a timing interval generator to generate a timing interval between an intermediate event and the timing reference event. This approach is applied when the intermediate event is more easily detectable than the timing reference event and when an approximate timing relationship between the intermediate event and the timing reference event is predictable. In an embodiment, the signal processor 219 processes the reference signal to provide for extraction of the timing reference event based on a plurality of cardiac cycles. In one specific embodiment, the signal processor 219 includes a signal averaging circuit that averages the reference signal over a predetermined number of cardiac cycles before the detection of the timing reference event by event detector 220.

The stimulation control circuit 210 may be a more specific embodiment of stimulation control circuit 110 and includes a synchronization circuit 211, and a dose control 213. The illustrated dose control 213 may include an offset interval generator 221 and a pulse delivery controller 222. The synchronization circuit 211 may include one or both of a continuous synchronization module 223 and a periodic synchronization module 224. The continuous synchronization module 223 synchronizes the delivery of the neural stimulation pulses to the timing reference event of consecutive cardiac cycles. A periodic synchronization module 224 synchronizes the delivery of the neural stimulation pulses to the timing reference event of selected cardiac cycles on a periodic basis. An offset interval generator 221 produces an offset interval starting with the detected timing reference event. A pulse delivery controller 222 sends the pulse delivery signal to start a delivery of a burst of a plurality of neural stimulation pulses when the offset interval expires. For example, the pulse delivery controller 222 may send the pulse delivery signal after the detection of the timing reference event for each of consecutive cardiac cycles. In an example, the pulse delivery controller 222 sends the pulse delivery signal after the detection of the timing reference event for selected cardiac cycles according to a predetermined pattern or programmed schedule, such as on a periodic basis. The illustrated system 201 may also include NS electrodes 104 for use in stimulating a neural target, communication circuitry 216 and memory 214 with programmed dose(s) 215 as generally illustrated and discussed with respect to FIG. 1. The illustrated system may also include physiological sensor(s) 207, activity sensor(s) 206, and an activity discriminator 212 as generally illustrated and discussed with respect to FIG. 1.

Figure 3:
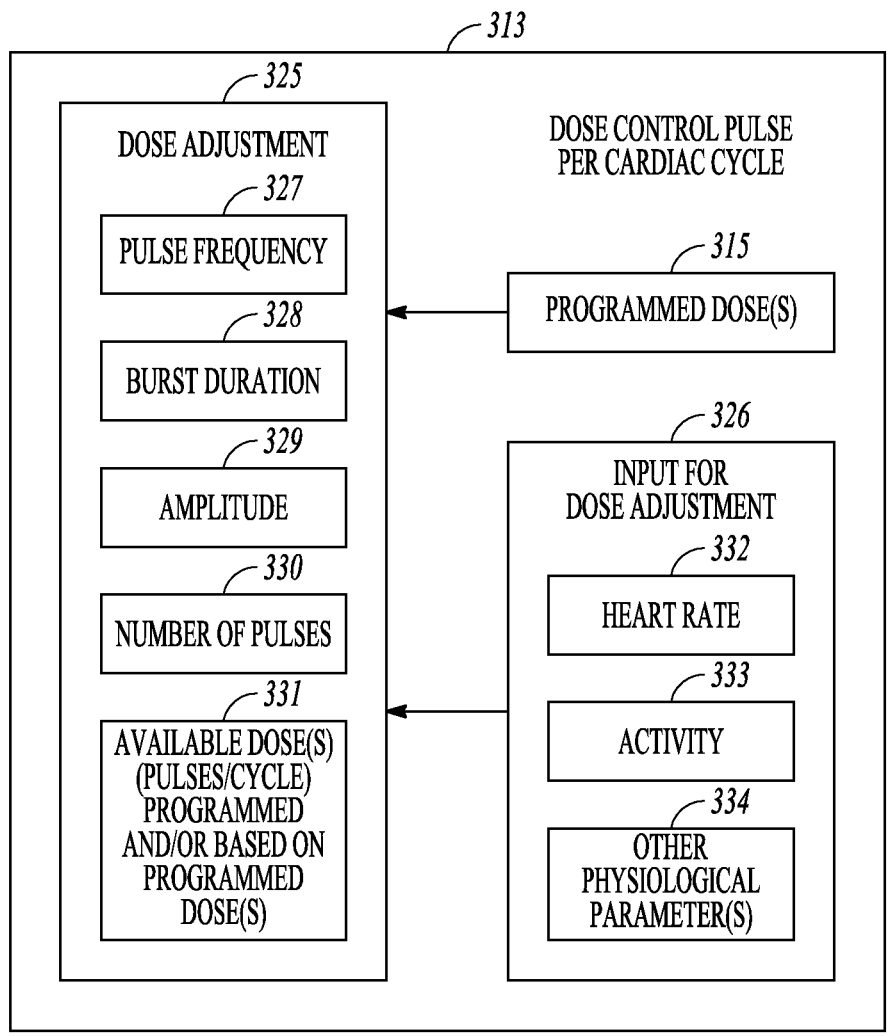
FIG. 3 illustrates an example of a dose control module, which may be specific example of a dose control module in FIG. 1 or FIG. 2.

FIG. 3 illustrates an example of a dose control module 313, which may be specific example of a dose control module 113 in FIG. 1 or a dose control module 213 in FIG. 2. The illustrated dose control module 313 uses the programmed dose 315 to control the number of pulses per cardiac cycle. The dose control module 313 may also include a dose adjustment module 325 for adjusting the programmed dose based on received input for the dose adjustment 326. For example, the dose control module 313 may be configured to change the pulses frequency 327 of the NS pulses delivered during a cardiac cycle, or the duration 328 of the burst of pulses delivered during a cardiac cycle, the amplitude 329 of the NS pulses delivered within the burst, or change the number of pulses per cardiac cycle 330. The dose adjustment module 325 may further be configured to control the allowable doses 331 that can be delivered during a cardiac cycle. For example, the number of pulses that may be delivered may be preprogrammed doses, or may be user-programmable doses. The number of pulses that may be delivered in a given cardiac cycle may be limited by a maximum number and/or limited by a minimum number. Further, limits (minimum and/or maximum) may be placed on the pulse frequency, the burst duration, and/or the amplitude. These limits may be programmed limits and/or may be derived from the programmed doses. For example, the system may be configured to determine the allowable range of doses based on a programmed maximum dose of NS pulses per cardiac cycle. Some system embodiments may use heart rate 332, and/or activity 333, and/or another physiological parameter 334 as an input to control the dose adjustment. In some embodiments, the system records the heart rate 332, and/or activity 333, and/or another physiological parameter 334 for communication to the second system to enable a user to review these measurements and adjust programming.

Figure 4:
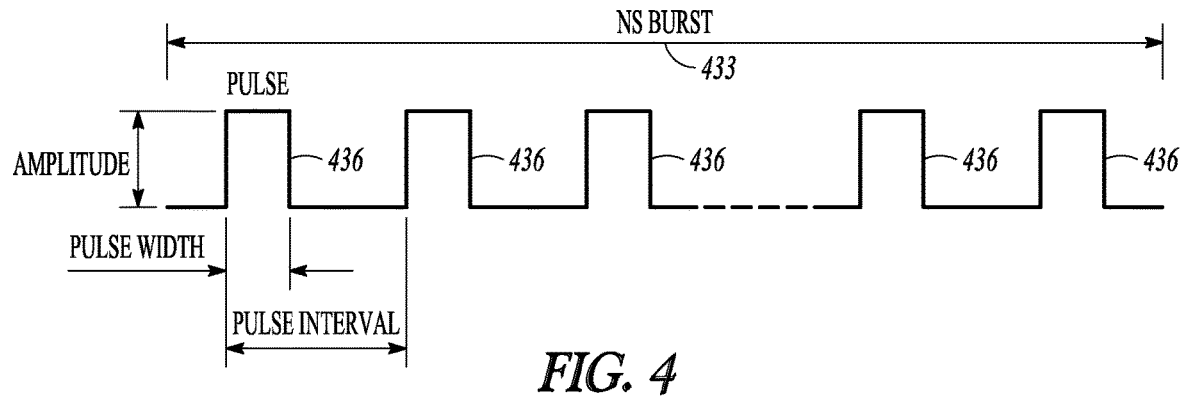
FIG. 4 illustrates, by way of example, an NS burst of NS pulses.

FIG. 4 illustrates an NS burst 435 of NS pulses 436. The NS burst 435 has a number of NS pulses 436, which can be delivered during a cardiac cycle and can define a NS dose of NS pulses per cardiac cycle. The NS pulses delivered within the burst may have a consistent pulse width and a repeated pulse interval. Those of ordinary skill in the art will appreciate that the pulse interval may be referred to as a pulse frequency as a pulse occurs after a period of time (e.g. pulse period=1/pulse frequency). The illustrated pulses also have an amplitude.

The intensity of neural stimulation is affected by the amount of charge delivered to the target, as well as the density of the charge delivered to the target during the period of time. This amount of charge depends on the amplitude, the pulses width, and the pulse frequency of the pulses affect the amount of delivered charge, and thus can affect the dose. This can become complicated to program and control, particularly for intermittent neural stimulation that may deliver NS bursts of NS pulses during an ON period of time and then deliver no neural stimulation during an OFF period of time. According to various embodiments, the dosing of the neural stimulation is characterized using the number of pulses per cardiac cycle. The amplitude of these NS pulses may be adjusted to further control the NS dose of the therapy.

Figure 5:
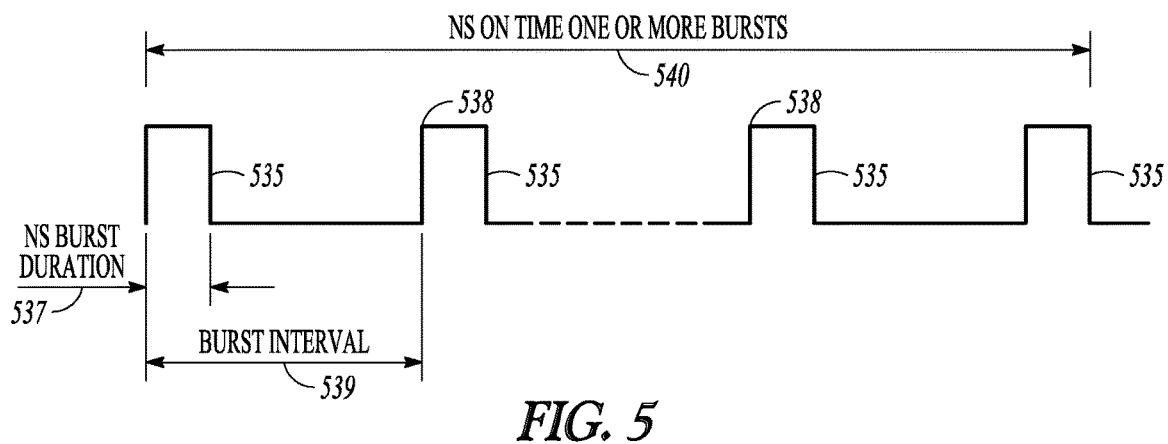
FIG. 5 illustrates, by way of example, a representation of intermittent neural stimulation (INS).

FIG. 5 illustrates a representation of intermittent neural stimulation (INS). The figure diagrammatically shows the time-course of a neural stimulation that alternates between intervals of stimulation being ON, when one stimulation pulse or a set of grouped stimulation pulses (i.e., a burst 535) is delivered, and intervals of stimulation being OFF, when no stimulation pulses are delivered. Thus, for example, some embodiments deliver a plurality of monophasic or biphasic pulses within a neural stimulation burst 435 illustrated in FIG. 4. The duration of the stimulation ON interval is sometimes referred to as the stimulation duration or burst duration 537. The burst duration also affects the dose of the neural stimulation therapy. The start of a stimulation ON interval is a temporal reference point NS Event 538. The NS Event may be a sensed event or derived from a sensed event or a programmed time. The time interval between successive NS Events is the INS Interval 539, which is sometimes referred to as the stimulation period or burst period. The burst period or the number of neural stimulation events that occur over a time period also affect the dose of the neural stimulation. For an application of neural stimulation to be intermittent, the stimulation duration 537 is less than the stimulation period (i.e., INS Interval 539). The duration of the OFF intervals of INS are determined by the durations of the ON interval and the INS Interval. The duration of the ON interval relative to the INS Interval (e.g., expressed as a ratio) is sometimes referred to as the duty cycle of the INS. The present subject matter may deliver a burst of NS pulses within a cardiac cycle, and may further deliver the burst of NS pulses timed to a desired time within the cardiac cycle. One or more bursts of NS pulses may be delivered during a NS ON time 540.

Figure 6:
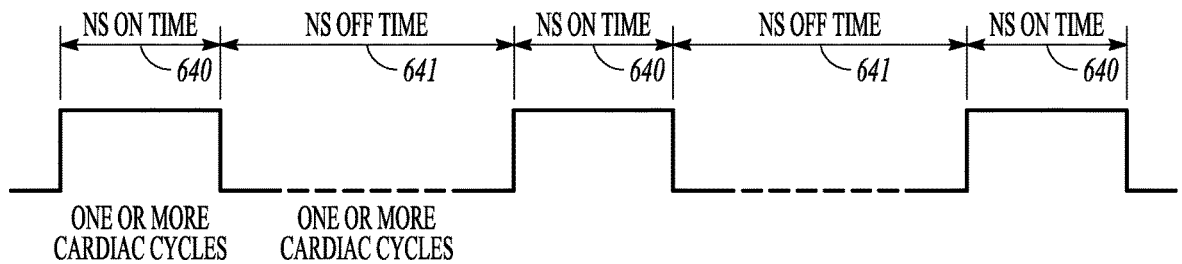
FIG. 6 illustrates, by way of example, a representation of an additional layer of ON/OFF timing for the neural stimulation.

FIG. 6 illustrates a representation of an additional layer of ON/OFF timing for the neural stimulation. By way of example and not limitation, the INS illustrated in FIG. 5 as being delivered during NS ON time 540 may be delivered during NS ON times 640 over one or more cardiac cycles. These NS ON times 640 are separated by NS OFF times 641 over one or more cardiac cycles without NS pulses.

Figure 7:
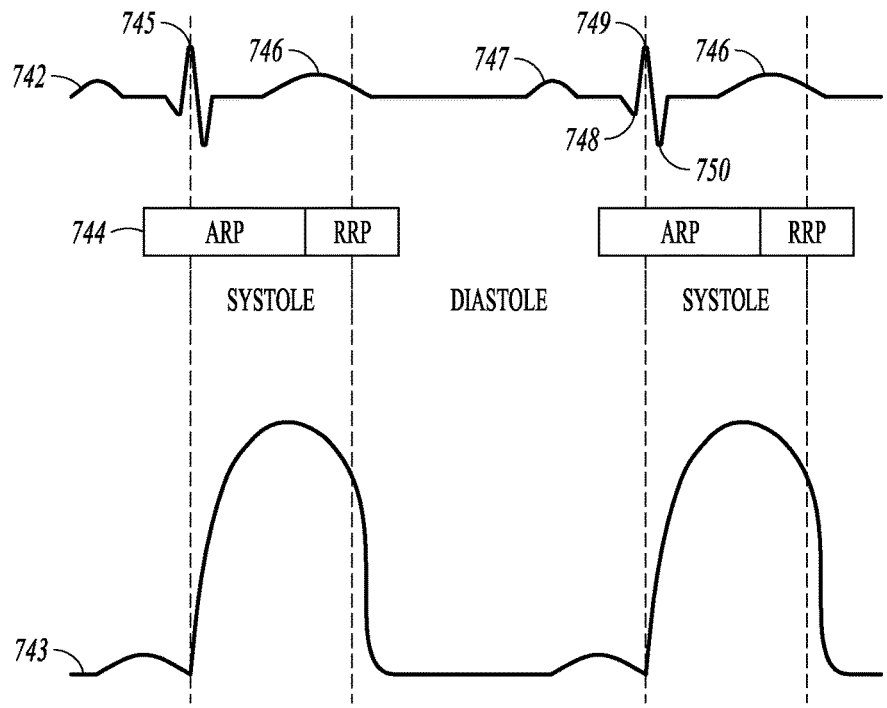
FIG. 7 illustrates, by way of example, a general relationship between an electrocardiogram (ECG), a pressure waveform within a blood vessel (e.g. pulmonary artery) and the refractory period of the heart during systolic and diastolic portions of a cardiac cycle.

FIG. 7 illustrates a general relationship between an electrocardiogram (ECG) 742, a pressure waveform 743 within a blood vessel (e.g. pulmonary artery) and the refractory period 744 of the heart during systolic and diastolic portions of a cardiac cycle. Systole is the portion of the cardiac cycle when the heart contracts to force blood through the circulatory system. Diastole is the portion of the cardiac cycle when the heart expands to fill with blood. Blood pressure increases during systole.

Figure 8:
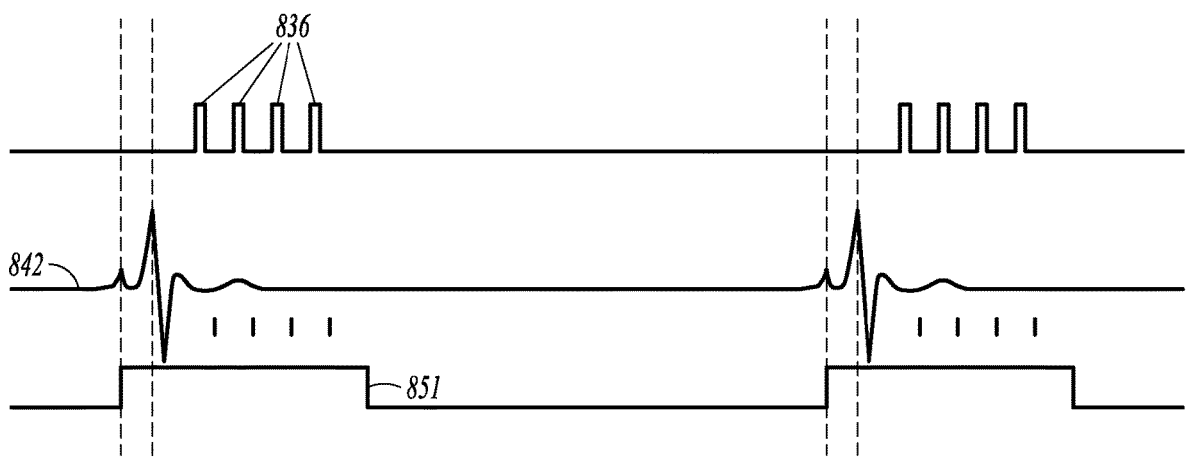
FIG. 8 illustrates an example of a NS burst of NS pulses delivered during an NS window that generally corresponds to at least a portion of the refractory period of the heart as illustrated by the ECG signal.

The cardiac refractory period 744 is separated into an absolute refractory period (ARP) and a relative refractory period (RRP). During the absolute refractory period, a new action potential cannot be elicited during the absolute refractory period but may be elicited with a greater than normal stimulus during the relative refractory period. The refractory period generally begins with the QRS waveform 745 and extends through the T wave 746. Various detectable cardiac events within the cardiac cycle may be used to tie the delivery of NS bursts. Examples of such detectable cardiac events include but are not limited to the P wave 747, Q wave 748, R wave 749, S wave 750 or T wave 746, or different detectable heart sounds for example. Some embodiments may time the delivery of the NS burst of NS pulses to occur during at least a portion of the refractory period (i.e. during at least a portion of the absolute and/or relative refractory periods). For example, baroreceptors sense pressure and elicit a baroreflex response. Neural stimulation to elicit a baroreflex response may be timed to occur during the refractory period to augment the natural baroreflex response. FIG. 8 illustrates an example of a NS burst of NS pulses 836 delivered during an NS window 851 that generally corresponds to at least a portion of the refractory period of the heart as illustrated by the ECG signal 842. In some embodiments, the delivery of the NS burst of NS pulses may be timed to occur during diastole to reduce the pulsation of the naturally-elicited baroreflex response.

Figure 9:
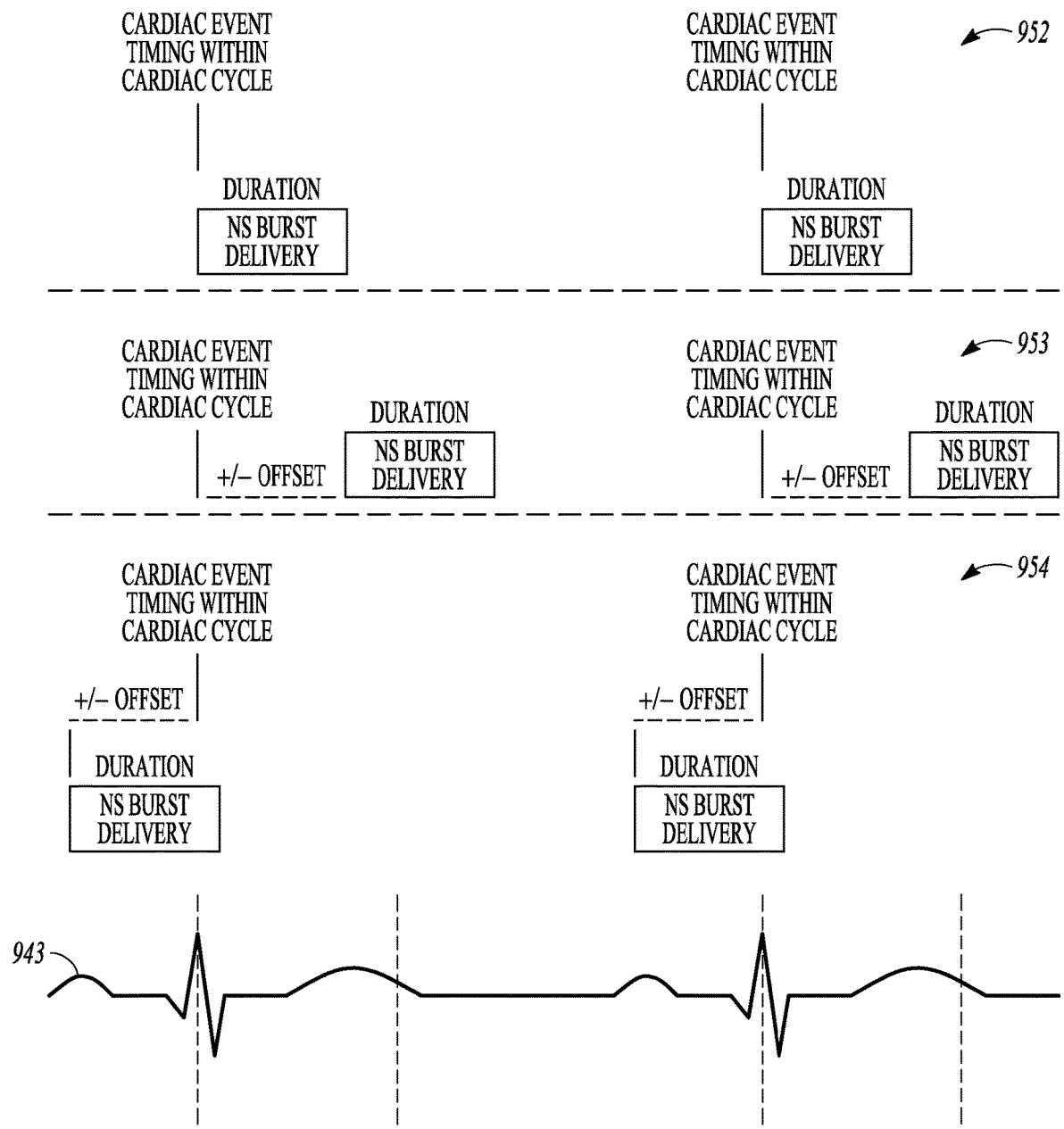
FIG. 9 illustrates, by way of example, some embodiments of NS burst timing.

FIG. 9 illustrates, by way of example and not limitation, some embodiments of NS burst timing. In a first example, the NS burst is delivered during a window of time beginning with the detected cardiac event. The initiation of the NS burst may begin with the detected cardiac cycle. In the illustrated examples, the cardiac event corresponds with the R wave 949 in the ECG signal 943. The duration of the NS burst may be a programmable parameter. In a second example, the NS burst is initiated an offset period of time after detection of the cardiac event. In a third example, the NS burst is initiated at offset period of time before the cardiac event.

Figure 10:
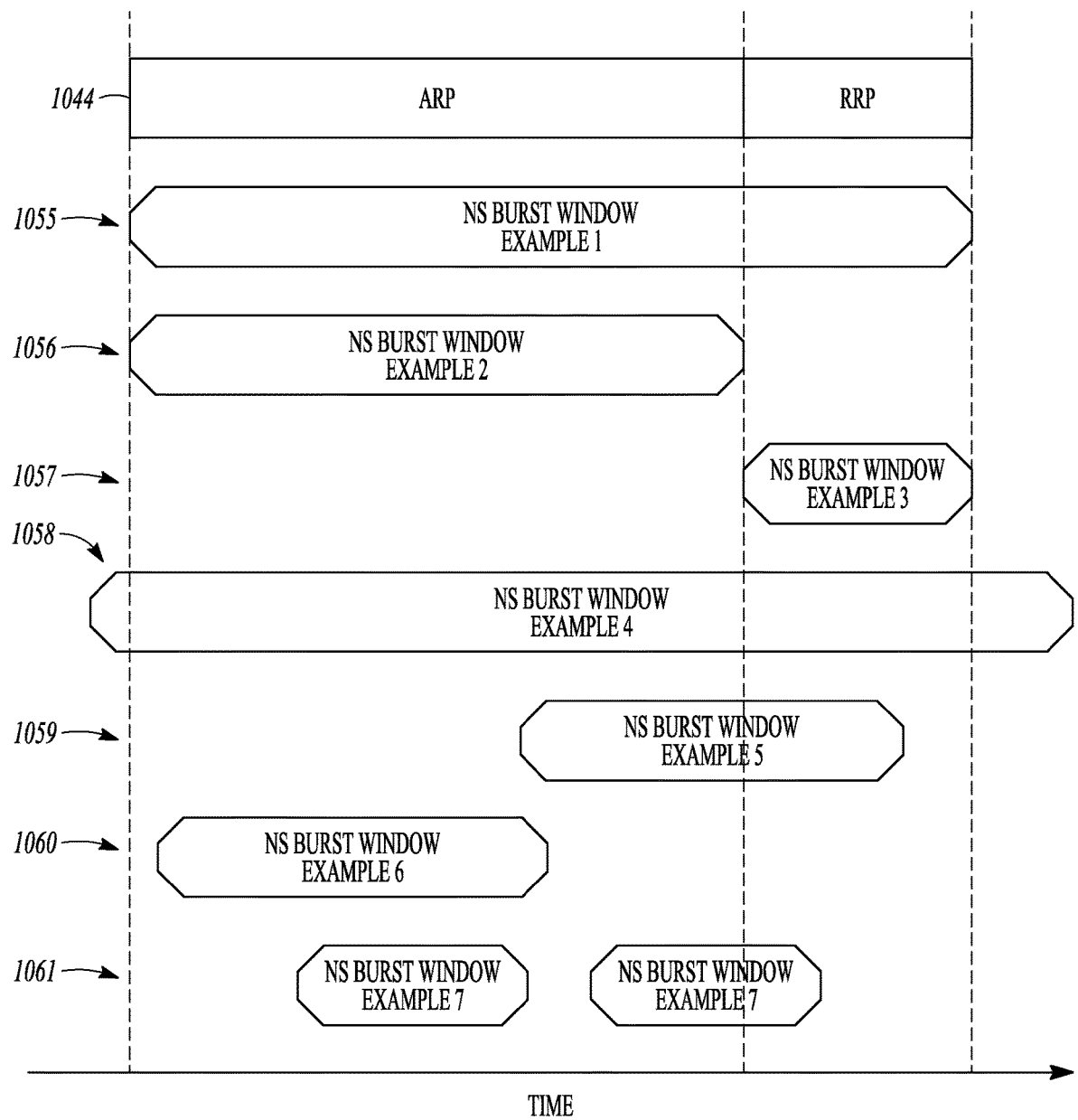
FIG. 10 illustrates, by way of example, some embodiments of NS burst timing with respect to the refractory period.

FIG. 10 illustrates some NS burst timing with respect to the refractory period 1044, by way of examples and not limitation. In a first example 1055, the NS burst window, within which the burst of NS pulses may be delivered, generally begins as the refractory period begins and ends when the refractory period ends. In a second example 1056, the NS burst window, within which the burst of NS pulses may be delivered, generally begins as the absolute refractory period beings and ends as the absolute refractory period ends. In a third example 1057, the NS burst window, within which the burst of NS pulses may be delivered, generally begins at the beginning of the relative refractory period and ends as the relative refractory period ends. In a fourth example 1058, the NS burst window, within which the burst of NS pulses may be delivered, may begin before the refractory period begins and/or may end after the refractory period ends. In a fifth example 1059, the NS burst window, within which the burst of NS pulses may be delivered, generally begins and ends within the refractory period. In the sixth example 1060, the NS burst window, within which the burst of NS pulses may be delivered, generally begins and ends within the absolute refractory period. In a seventh example 1061, more than one NS burst window may be provided within the refractory period.

Figure 11:
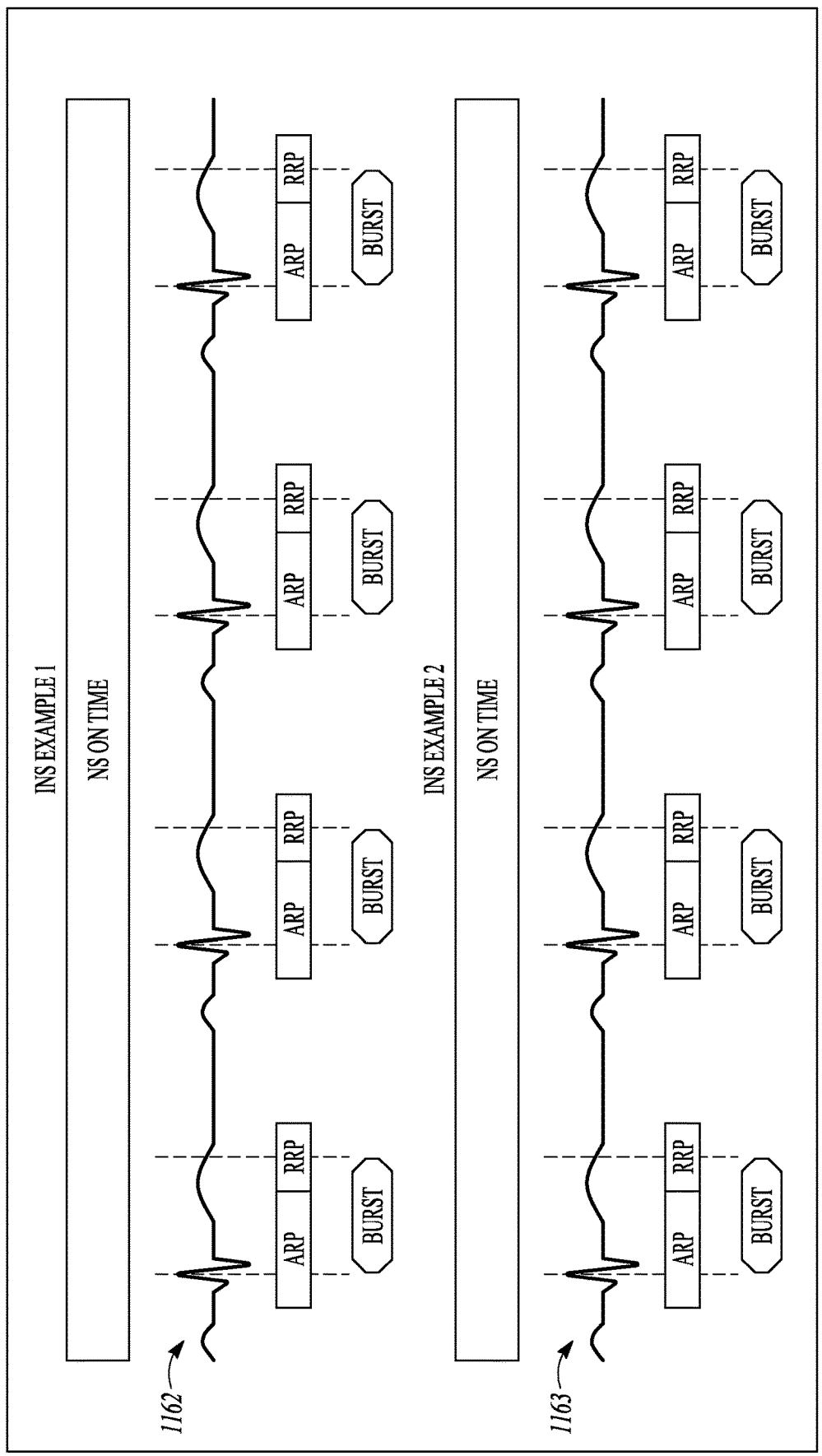
FIG. 11 illustrates, by way of example, some NS burst timing with respect to cardiac cycles.

FIG. 11 illustrates some NS burst timing with respect to cardiac cycles. In a first example 1162, a NS burst of NS pulses is delivered during every cardiac cycle. In a second example 1163, a NS burst of NS pulses is delivered only is some of the cardiac cycles, and is not delivered in other cycle. For example, the NS burst may be delivered every other cardiac cycle. The determination of which cardiac cycles within which to deliver a NS burst may be based on a timer. For example, after expiration of a timer a NS burst may be delivered during each of the next one or more cardiac cycles; or after expiration of a timer a pattern of cardiac cycles a NS burst may be delivered for a pattern of cardiac cycles (e.g. every N cardiac cycles). The determination of which cardiac cycles within which to deliver a NS burst may be based on a sensed physiological parameter.

Figure 12:
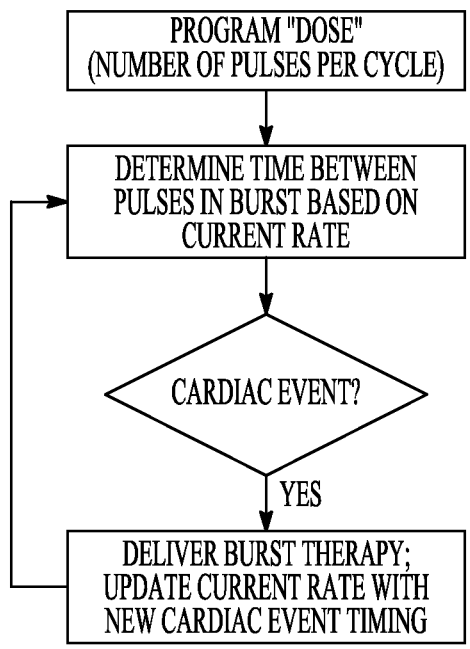
FIGS. 12-14 illustrate, by way of example, various embodiments for delivering a NS burst of pulses during a cardiac cycle.
Figure 13:
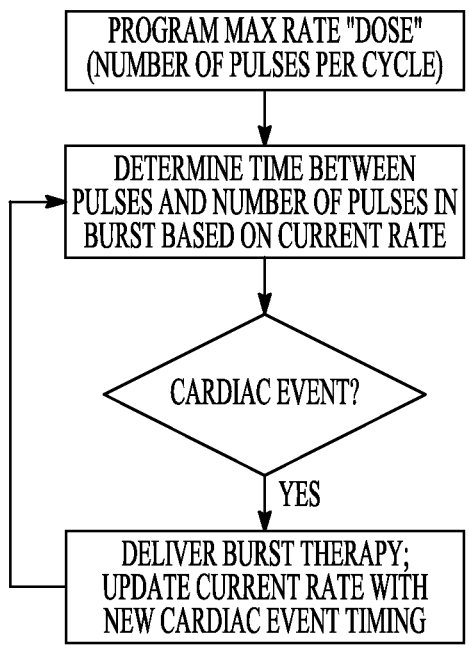
Figure 14:
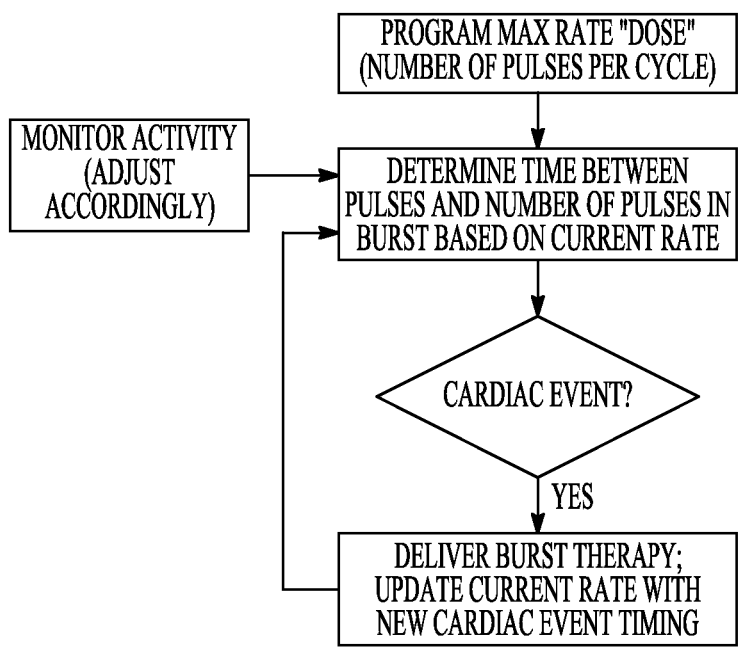

FIGS. 12-14 illustrate various embodiments for delivering a NS burst of pulses during a cardiac cycle. These processes may be implemented, for example, using any of the systems illustrated in FIGS. 1-3. The processes may be implemented using hardware, software and/or firmware.

In FIG. 12, an NS dose may be programmed into the system. For example, the programmed dose may be stored in memory 114 or 214. The dose may be programmed as a number of pulses per cardiac cycle, or may be programmed as a combination of the number of pulses per cycle and the amplitude of the pulses. The current cardiac rate may be measured a variety of ways. By way of example and not limitation, a heart rate sensor, an ECG sensor, a heart sound sensor, a blood pressure sensor, or a blood flow sensor may be used to determine a cardiac rate. The current cardiac rate is used to determine or update the timing between NS pulses ("NS pulse frequency"). Upon detection of a cardiac event, the NS burst is delivered using the updated NS pulse frequency.

In FIG. 13, a maximum dose is programmed into the system. The dose may be programmed as a number of pulses per cardiac cycle, or may be programmed as a combination of the number of pulses per cycle and the amplitude of the pulses. The current cardiac rate may be measured and used to determine or update the timing between NS pulses ("NS pulse frequency") and/or may be used to modify the number of pulses in the burst without exceeding the programmed maximum dose. Upon detection of a cardiac event, the NS burst is delivered using the updated NS pulse frequency.

In FIG. 14, a maximum dose is programmed into the system. The dose may be programmed as a number of pulses per cardiac cycle, or may be programmed as a combination of the number of doses and number of pulses. The current cardiac rate may be measured and used to determine or update the timing between NS pulses ("NS pulse frequency") and/or may be used to modify the number of pulses in the burst without exceeding the programmed maximum dose. Furthermore, the patient's activity may be monitored, and this monitored activity may be used as a factor in determining or updating timing between NS pulses ("NS pulse frequency") and/or may be used to modify the number of pulses in the burst. The patient's activity may be monitored using sensor(s) such as, but not limited to, accelerometer-based sensors, heart rate sensors, blood pressure sensors, and/or respiration sensors. A discriminator can determine the patient's activity level based on the output(s) from such sensor(s). Upon detection of a cardiac event, the NS burst is delivered using the updated NS pulse frequency.

The above detailed description is intended to be illustrative, and not restrictive. Other embodiments will be apparent to those of ordinary skills in the art upon reading and understanding the above description. The scope of the disclosure should, therefore, be determined with references to the appended claims, along with the full scope of equivalents to which such claims are entitled.

What is claimed is:

1. A method, comprising:

using a neural stimulation system to deliver a neural stimulation therapy by delivering neural stimulation pulses including more than one neural stimulation pulse over a period of time, wherein the neural stimulation system includes a first system configured to deliver the neural stimulation pulses for the neural stimulation therapy and a second system configured to program the first system to deliver the neural stimulation therapy, and the second system includes a display and a dose programming interface configured for use by a user of the second system to program the first system to deliver the neural stimulation pulses for the neural stimulation therapy;

determining a neural stimulation dose for the neural stimulation therapy by determining, using the neural stimulation system, a total charge for the more than one neural stimulation pulse over the period of time; and displaying a dose meter on the display of the second system, wherein the dose meter provides an indicator of the neural stimulation dose for the neural stimulation therapy, enabling the user of the second system to receive dose information for either a current user-programmable neural stimulation dose for the neural stimulation therapy that corresponds to currently-programmed stimulation parameters in the first system or a user-proposed neural stimulation dose that corresponds to proposed stimulation parameters for the neural stimulation therapy before the user programs the first system with the proposed neural stimulation parameters.

2. The method of claim 1, wherein the indicator is for the current user-programmable neural stimulation dose for the neural stimulation therapy.

3. The method of claim 1, wherein the indicator is for the user-proposed neural stimulation dose for the neural stimulation therapy.

4. The method of claim 1, wherein the indicator is for both the current user-programmable neural stimulation dose and the user proposed neural stimulation dose.

5. The method of claim 1, wherein the neural stimulation dose includes the user programmable neural stimulation dose, the method further comprising providing instructions to the neural stimulation system for use by the neural stimulation system to deliver the user programmable neural stimulation dose of the neural stimulation therapy.

6. The method of claim 1, further comprising
sensing a physiological parameter and changing the neural stimulation dose based on the sensed physiological parameter.

7. The method of claim 6, wherein the sensed physiological parameter is indicative of heart rate changes, wherein the neural stimulation dose is changed by increasing the neural stimulation dose when the sensed physiological parameter indicates a decreased heart rate.

8. The method of claim 6, wherein the sensed physiological parameter is indicative of heart rate changes, wherein the neural stimulation dose is changed by increasing the neural stimulation dose when the sensed physiological parameter indicates an increased heart rate.

9. The method of claim 6, further comprising implementing a rate smoothing algorithm to slow a response time to a change in the sensed physiological parameter.

10. A neural stimulation system, comprising:
a first system configured to deliver neural stimulation pules, including more than one neural stimulation pulse over a period of time, for a neural stimulation therapy; and
a second system configured to program the first system to deliver the neural stimulation therapy, the second system including a display and a dose programming interface configured for use by a user of the second system to program the first system to deliver the neural stimulation pulses for the neural stimulation therapy,
wherein the neural stimulation system is configured to determine a neural stimulation doses for the neural stimulation therapy by determining, using the neural stimulation system, a total charge for the more than one neural stimulation pulse over the period of time,
wherein the second system is configured to display a dose meter on the display, wherein the dose meter provides an indicator of the neural stimulation dose for the neural stimulation therapy, enabling the user of the second system to receive dose information for either a current user-programmable neural stimulation dose for the neural stimulation therapy that corresponds to currently-programmed stimulation parameters in the first system or a user-proposed neural stimulation dose that corresponds to proposed stimulation parameters for the neural stimulation therapy before the user programs the first system with the proposed neural stimulation parameters.

11. The system of claim 10, wherein the indicator is for the current user-programmable neural stimulation dose.

12. The system of claim 10, wherein the indicator is for the user-proposed neural stimulation dose.

13. The system of claim 10, wherein the indicator is for both a current user-programmable dose and the user-proposed dose.

14. The system of claim 10, wherein the second system is configured for use by a user to program a value for a programmable neural stimulation dose, and the first system includes a controller configured to control delivery of the programmable neural stimulation dose of the neural stimulation therapy.

15. A non-transitory machine-readable medium including instructions, which when executed by a machine having a display, cause the machine to provide a method comprising:
using a neural stimulation system to deliver a neural stimulation therapy by delivering neural stimulation pulses including more than one neural stimulation pulse over a period of time, wherein the neural stimulation system includes a first system configured to deliver the neural stimulation pulses for the neural stimulation therapy and a second system configured to program the first system to deliver the neural stimulation therapy, and the second system includes a display and a dose programming interface configured for use by a user of the second system to program the first system to deliver the neural stimulation pulses for the neural stimulation therapy;
determining a neural stimulation dose for the neural stimulation therapy by determining, using the neural stimulation system, a total charge for the more than one neural stimulation pulse over the period of time; and
displaying a dose meter on the display of the second system, wherein the dose meter provides an indicator of the neural stimulation dose for the neural stimulation therapy, enabling the user of the second system to receive dose information for either a current user-programmable neural stimulation dose for the neural stimulation therapy that corresponds to currently-programmed stimulation parameters in the first system or a user-proposed neural stimulation dose that corresponds to proposed stimulation parameters for the neural stimulation therapy before the user programs the first system with the proposed neural stimulation parameters.

16. The non-transitory machine-readable medium of claim 15, wherein the instructions include instructions, which when executed by the machine, cause the machine to sense a physiological parameter and change the neural stimulation dose based on the sensed physiological parameter.

17. The non-transitory machine-readable a medium of claim 16, wherein the sensed physiological parameter is indicative of heart rate changes, wherein the neural stimulation dose is changed by increasing the neural stimulation dose when the sensed physiological parameter indicates a decreased heart rate.

18. The non-transitory machine-readable medium of claim 16, wherein the sensed physiological parameter is indicative of heart rate changes, wherein the neural stimulation dose is changed by increasing the neural stimulation dose when the sensed physiological parameter indicates an increased heart rate.

19. The non-transitory machine-readable medium of claim 16, wherein the method further comprises a rate smoothing algorithm to slow a response time to a change in the sensed physiological parameter.

20. The non-transitory machine-readable medium of claim 16, wherein the indicator is for both the current user programmable neural stimulation dose and the user-proposed neural stimulation dose.

* * * * *